(12) United States Patent
McQuaid (10) Patent No.: US 6,962,633 B1
(45) Date of Patent: Nov. 8, 2005

(54) AMINE AZIDE PROPELLANT

(75) Inventor: Michael J. McQuaid, Bel Air, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 248 days.

(21) Appl. No.: 10/389,885

(22) Filed: Mar. 18, 2003

(51) Int. Cl.[7] .................. C06B 47/00; C06B 47/04; C06B 47/02; C07C 247/14; C07D 203/06
(52) U.S. Cl. ................... 149/1; 149/22; 149/17; 149/45; 149/74; 149/109.4; 44/265; 544/111; 544/141; 544/166; 548/557; 548/558; 548/953; 548/965; 549/480; 549/510; 549/550; 552/1
(58) Field of Search .................. 149/1, 17, 22, 149/45, 74, 109.4; 44/265; 544/111, 141, 544/166; 548/557, 558, 953, 965; 549/480, 549/510, 550; 552/1

(56) References Cited

U.S. PATENT DOCUMENTS

| 3,886,118 | A | 5/1975 | Nitzsche et al. | 260/46.5 |
|---|---|---|---|---|
| 3,971,681 | A | 7/1976 | Rains et al. | 149/19.8 |
| 4,223,122 | A | 9/1980 | Cella | 528/30 |
| 4,432,815 | A | 2/1984 | Frankel et al. | 149/19.3 |
| 6,013,143 | A | 1/2000 | Thompson | 149/1 |
| 6,210,504 | B1 | 4/2001 | Thompson | 149/1 |
| 6,299,654 | B1 | 10/2001 | Thompson | 44/265 |

*Primary Examiner*—Bernard Dentz
(74) *Attorney, Agent, or Firm*—William V. Adams (57) ABSTRACT

A novel family of amine azides having a cyclic structure therein is disclosed. These compounds have attractive properties as rocket propellants.

25 Claims, 5 Drawing Sheets

AMINE AZIDE PROPELLANT

GOVERNMENT INTEREST

The invention described herein may be manufactured, used, and licensed by or for the United States Government.

FIELD OF THE INVENTION

The present invention generally relates to cyclic compounds with amine and azide functional groups, and in particular to cyclic compounds with amine and azide functional groups suitable as hypergolic fuel components.

BACKGROUND OF THE INVENTION

Hypergolic propellants are characterized by spontaneous reaction upon component mixing and high energy yield per unit mass. As a result of these characteristics, hypergolic propellants are commonly used to power spacecraft, tactical missiles and reactive thruster controllers.

Many conventional hypergolic fuel-oxidizer combinations have the desirable properties of high energy density per unit mass, high specific impulse and short ignition delays. Unfortunately, many of the hypergolic fuels having these properties are derived from hydrazine and include monomethylhydrazine (MMH), unsymmetrical dimethylhydrazine, or combinations thereof. As hydrazines as a class are acutely toxic and suspected carcinogens, costly safety precautions and handling procedures are required. (E. W. Schmidt. *Hydrazine and Its Derivatives: Preparation, Properties, and Applications*. New York, N.Y.: John Wiley & Sons, Inc., 2001).

Various 2-azidoethanamines have been synthesized and evaluated as potential non-carcinogenic hypergolic fuel compounds. (D. M. Thompson et al. "Hypergolic Azide Liquid Fuels." *Proceedings of the 1998 JANNAF Propulsion Meeting*, CPIA Publication 675, vol. III, pp. 515–523, 1998.). Within the class of 2-azidoethanamines, 2-azido-N,N-dimethylethanamine (DMAZ), having the structure $(CH_3)_2NCH_2CH_2N_3$, appears to be one of the better candidates. DMAZ yields performance comparable to a fifty—fifty mixture by weight of hydrazine and unsymmetrical dimethylhydrazine in inhibited red fuming nitric acid (IRFNA) oxidized experimental systems. However, DMAZ-IRFNA systems do not meet higher performance standards set by monomethylhydrazine-IRFNA systems, the primary shortcoming being a longer ignition delay. A longer ignition delay results in a greater accumulation of unreacted propellant in the combustion chamber prior to ignition. When the unreacted propellant finally ignites, it produces a pressure transient proportional to the amount accumulated. Therefore, to avoid rupturing the combustion chamber, the chamber must be sized to accommodate the expected transient. Since rocket performance is degraded by larger combustion chamber sizes, shorter ignition delays, leading to smaller propellant accumulations, are desirable. To date, the class of 2-azidoethanamines has not yielded an acceptable substitute for hydrazine-based hypergolic propellants. Thus, there still exists a need for a non-carcinogenic fuel that has energy density, specific impulse and ignition delay characteristics associated with hydrazine compounds.

SUMMARY OF THE INVENTION

An inventive compound includes an azide group pendant from a cyclic group that has amine functionality therein or pendant thereto. The cyclic group including epoxy, cyclopropyl, cyclobutyl, cyclopentyl, azetidyl, aziridyl, and substituted forms thereof where hydrogen atoms are substituted by methyl or ethyl groups in each occurrence. Based on an understanding of propellant properties for inventive compounds, a propellant is readily formulated from a single inventive compound, inventive isomer, or a mixture of such compounds, or isomers with desired properties such as being hypergolic, of a high specific impulse, or of a high-density impulse. An inventive propellant includes an inventive compound and an oxidation or ignition source.

DESCRIPTION OF THE PREFERRED EMBODIMENTS

The present invention has utility as a hypergolic fuel compound. The present invention is based on a finding that in the 2-azido-N,N-dimethylethanamine lowest energy configuration the azide group sterically shields the lone pair electrons associated with the amine nitrogen. (M. J. McQuaid, K. L McNesby, B. M. Rice, and C. Chabawoloski, "Density functional theory characterization of the structure and gas-phase, mid-infrared absorption spectrum of 2-azido-N,N-dimethylethanamine (DMAZ)." *Journal of Molecular Structure (Theochem)*, vol. 587, pp. 199–218, 2002). The present invention thus provides compounds that are tailored to either enhance or limit intramolecular interaction between an azide group and an amine nitrogen lone pair of electrons.

The present invention relates to a class of cyclic compounds with amine and azide functional groups of the formula:

(I)

where A is $CHR^1$, O, $CHR^1CHR^1$, $CHN(R^2)_2CH_2$, $CHR^1CHR^1CHR^1$, $NR^2CH_2CHR^1$, $CHR^1CH_2NR^2$, $CH_2NR^2CH_2$, $NR^2$, $NR^2CH_2$, $CH_2NR^2$, $CH_2O$, $OCH_2$, $OCH_2CH_2$, or $CH_2OCH_2$; $R^1$ in each occurrence is independently H or $N(R^2)_2$; $R^2$ in each occurrence is independently H, $CH_3$, or $CH_2CH_3$; $R^3$ is H, $N(R^2)_2$, where Z is CH or N; and a dashed bond denotes single bonds that when $R^3$ is $N(R^2)_2$, gives the compound a cis or trans orientation. As used herein, inventive compounds are defined to include a molecule including at least one azide group, at least one amine group, regardless of whether the amine is primary, secondary or tertiary, and also including a cyclic group including epoxy, cyclopropyl, cyclobutyl, cyclopentyl, azetidyl, aziridyl, and substituted forms thereof where hydrogen atoms are substituted by methyl or ethyl groups. It is appreciated that other three to five member cyclic structures having a core composed of carbon, nitrogen and oxygen atoms or carbon and oxygen atoms are also operative herein. Preferably, the electron density associated with a cyclic group of an inventive compound increases the reactivity of an amine group lone pair of electrons. As a result, in formulating a hypergolic fuel propellant, ignition characteristics are optionally tailored by adjusting the ratio of cis to trans forms of a given inventive compound as well as mixing inventive compounds having different cyclic groups. For example, inventive azidocycloalkanamines can be tailored to be stoichiometrically similar to the prior art 2-azido-N,N-dimethylethanamine (DMAZ) structure.

A propellant of the present invention includes a compound of Formula (I) and an oxidant. Oxidants illustratively include liquid oxygen, hydrogen peroxide, nitric acid, nitrogen dioxide, and inhibited red fuming nitric acid. Optionally, a catalyst is present in either the inventive compound or oxidant prior to mixing. It is appreciated that the presence of an igniter facilitates exothermic molecular decomposition of an inventive compound independent of the presence of an oxidizer.

Inventive compounds are synthesized through a variety of conventional synthetic routes. The preparation of azide compounds is well known in the art. (E. F. Schriven et al. "Azides: Their Preparation and Synthetic Uses." *Chemical Reviews*, vol. 88, pp. 297–368, 1988). A preferred synthesis of inventive compounds involves reacting a suitable amino alcohol with triphenylphosphorous, diethyl azodicarboxylate and hydrazoic acid. (A. Benalil et al. "Synthesis of 1,2-aminoazides. Conversion to Unsymmetrical Vicinal Diamines by Catalytic Hydrogenation or Reductive Alkylation with Dichloroboranes." *Tetrahedron*, vol. 47, p. 8177, 1991). This reaction is appreciated to be a modification of the Mitsunobu reaction. (H. Loibner et al. "Reactions with Organophosphorous Compounds. 41. New Preparative Methods using Triphenylphosphine-Diethyl azodicarboxylate-Hydroxy-compound." *Helvetica Chemica Acta*, vol. 59, pp. 2100–2113, 1976). Treatment of a suitable amino alcohol with $(PhO)_2P(O)N_3$ and triethylamine can be employed for precursors with acid sensitive rings. (Stevenson, W. H., *Proceedings of the 30th JANNAF Propellant Development and Characterization Subcommittee Meeting*, CPIA Publication 708, Vol. II, pp 95–102, 2002.) The synthesis of trans-2-hydroxy-N,N-dimethylcyclopropanamine is known to the art. (P. D. Armstrong et al. "Small Ring Analogs of Acetylcholine. Synthesis and Configurations of Cyclopropane Derivatives." *Journal of Medicinal Chemistry*, vol. 13, pp. 1037–1039, 1970). This represents a suitable reagent for the creation of 2-azido-N,N-dimethylcyclopropananamine. It is appreciated that other reaction schemes are operative to form an azide group including reaction of an organo halide with sodium azide. Optionally, an existing amine group is protected with a protecting group such as diterbutyldicarbonate (BOC). Additionally, the synthesis of chiral aziridines is known. (a) Z. Li et al. *J. Am. Chem. Soc.*, vol. 115, p. 5326, 1993; b) D. A. Evans et al., *J. Am. Chem. Soc.*, vol. 115, p. 5326, 1993; c) P. Dauban et al. *J. Org. Chem.*, vol. 60, p. 2035, 1995; d) N. J. Church et al. *Tetrahedron Lett.*, vol. 36, p. 151, 1995; e) M. E. Solomon et al., *Tetrahedron Lett.*, vol. 36, p. 4955, 1995; f) T. Ibuka et al.,*J. Org. Chem.*, vol. 60, p. 2044, 1995; g) S. Patai. *The Chemistry of the Azide Group*, Interscience Publishers, New York, 1971).

In order to assess the properties of the present invention, a series of theoretical computations were conducted. Theoretical structural and thermodynamic properties of inventive compounds attest to the utility of the present invention in designing a propellant.

In formulating a rocket propellant from an inventive compound, compound isomer, compound racemic mixture, or mixture of multiple inventive compounds, it is appreciated that a propellant gel often has desirable handling properties. To form a propellant gel according to the present invention, 0.5% to 10% gellant is optionally added. Gellants illustratively include silicon dioxide, clay, carbon, or any polymeric gellant that is nonreactive with an inventive compound. Optionally, a propellant gel according to the present invention includes one or more additives to improve the specific impulse and density impulse of the propellant. Such additives illustratively include amine-nitrate salts, quaternary ammonium salts such as tetramethyl ammonium azide, and nitro-substituted aromatics such as triamino trini trobenzene, aluminum, silicon, boron, and tungsten. Typically, a gelled propellant fuel includes such additives in from 1 to 90 total weight percent.

In order to more fully demonstrate the advantages arising from the present invention, the following examples are set forth. It is to be understood that the following is by way of example only and not intended as a limitation on the scope of the invention.

EXAMPLE 1

Computational Quantum Chemistry Results for 2-azido-N,N-dimethylcyclopropanamine (ADMCPA)

The Gaussian 98 (G98) suite of quantum chemistry codes (M. J. Frisch et al., *Gaussian* 98, Revision A.4., Gaussian, Inc., Pittsburgh, Pa. 1998.) is employed to identify equilibrium 2-azido-N,N-dimethylcyclopropanamine (ADMCPA) structures and characterize their normal modes. Density functional theory utilizing the B3LYP exchange-correlation functionals (A. D. Becke "Density-functional Thermochemistry.3. The Role of Exact Exchange." *Journal of Chemical Physics*, vol. 98, pp. 5684–5652, 1993; C. Lee et al. "Development of the Colle-Salvetti Correlation-Energy Formula Into a Functional of the Electron-Density." *Physical Review B*, vol. 37, pp. 785–789, 1988; B. Miehlich et al. "Results Obtained With The Correlation-Energy Density Functionals Of Becke And Lee, Yang And Parr." *Chemical Physics Letters*, vol. 157, pp. 200–206, 1989) and 6-311++G(d,p) atomic orbital basis set (T. Clark et al., "Efficient Diffuse Function-Augmented Basis-Sets for Anion Calculations. 3. The 3-21+G Basis Set for $1^{st}$-Row Elements, Li—F." *Journal of Computational Chemistry*, vol. 4, pp. 294–301, 1983; A. D. McLean et al. "Contracted Gaussian-Basis Sets For Molecular Calculations. 1. $2^{nd}$ Row Atoms, Z=11–18." *Journal of Chemical Physics*, vol. 72, pp. 5639–5648, 1980; R. Krishnan et al. "Self-Consistent Molecular-Orbital Methods. 20. Basis Sets for Correlated Wave-Functions." *Journal of Chemical Physics*, vol. 72, pp. 650–654, 1980) on a G98-defined "ultrafine" grid is employed for this purpose based on the success achieved with it in characterizing DMAZ (M. J. McQuaid, K. L McNesby, B. M. Rice, and C. Chabawoloski, "Density functional theory characterization of the structure and gas-phase, mid-infrared absorption spectrum of 2-azido-N,N-dimethylethanamine (DMAZ)." *Journal of Molecular Structure (Theochem)*, vol. 587, pp. 199–218, 2002). In addition to the structural characterizations, gas-phase heats of formation at 298 K [ΔH$_f$(298)] are estimated and used to predict ballistic performance. The results presented in Table 1 are derived from the heats of reaction [ΔH$_r$(0)] calculated for "isodesmic" reactions at 0 K in which the total number of each type of bond are equal in reactants and products. In an attempt to identify if the method generated systematic errors, a variety of reactions involving the formation of molecules of interest and $xH_2$ (x=1 or 2) from reactants with accepted ΔH$_f$(298) values are constructed and the ΔH$_f$(298) predictions compared. The zero-point corrected energies and enthalpy differences at 298 K and 0 K [H(298)—H(0)] for the reactants and reference elements needed to derive ΔH$_f$(298) from ΔH$_r$(0) are completed at the same level of theory as that employed to characterize the amine azides of interest.

TABLE 1

Calculated Fuel Properties and a Comparison of Optimized Performance When Oxidized with IRFNA

| Compound | ΔH$_{f,g}$(298) (kcal/mol) | ρ (g/cc) | ΔH$_v$(298) (kcal/mol) | $I_{SP}^a$ (sec) Exit | $D^*I_{SP}^b$ (lb$_m$ · sec/in$^3$) |
|---|---|---|---|---|---|
| MMAZ | 78.8 | 0.989 | 11.2 | 285.4 | 10.2 |
| DMAZ | 78.8 | 0.936 | 10.5 | 284.2 | 9.6 |
| CPAZ | 103.4 | 1.003 | 12.2 | 284.5 | 10.3 |
| trans-ADMCPA | 106.7 | 0.952 | 10.5 | 285.2 | 9.8 |
| cis-ADMCPA | 108.4 | 0.991 | 11.8 | 285.3 | 10.2 |
| MMH$^c$ | 22.7 | 0.88 | 9.6 | 288.1 | 9.2 |

[a] Results for "infinite-area" combustor problem with 2000 psia chamber pressure and equilibrium chemistry. The subsonic area ratio is 15.0 and the supersonic area ratio is 14.175.
[b] For consistency, in all cases except MMH, the density predictions obtained via the molecular modeling computations are employed to calculate $D^*I_{SP}$.
[c] Heat of formation, density and heat of vaporization for MMH are from E. W. Schmidt. Hydrazine and Its Derivatives: Preparation, Properties, and Applications. New York, NY: John Wiley & Sons, Inc., 2001.

Figure 1:
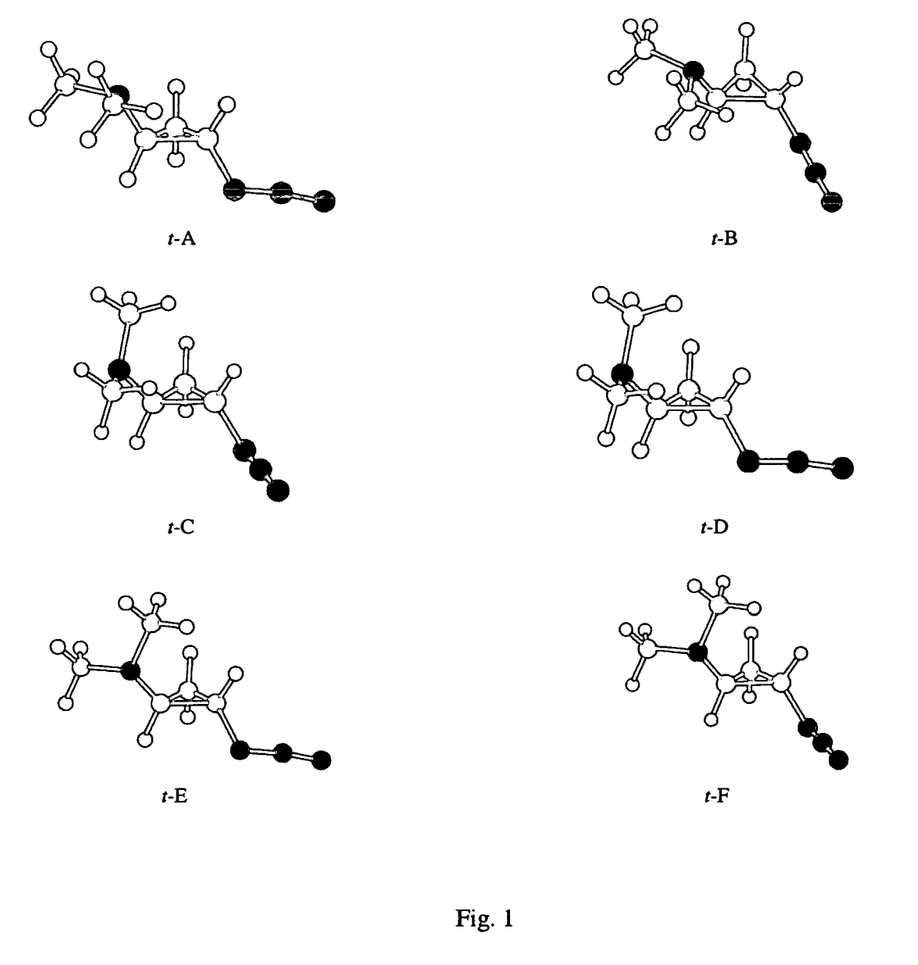
FIG. 1 depicts molecular structures of equilibrium trans-2-azido-N,N-dimethylcyclopropanamine (ADMCPA) conformers, black circles denoting nitrogen atoms, gray circles denoting carbon atoms and white circles denoting hydrogen atoms.
Figure 2:
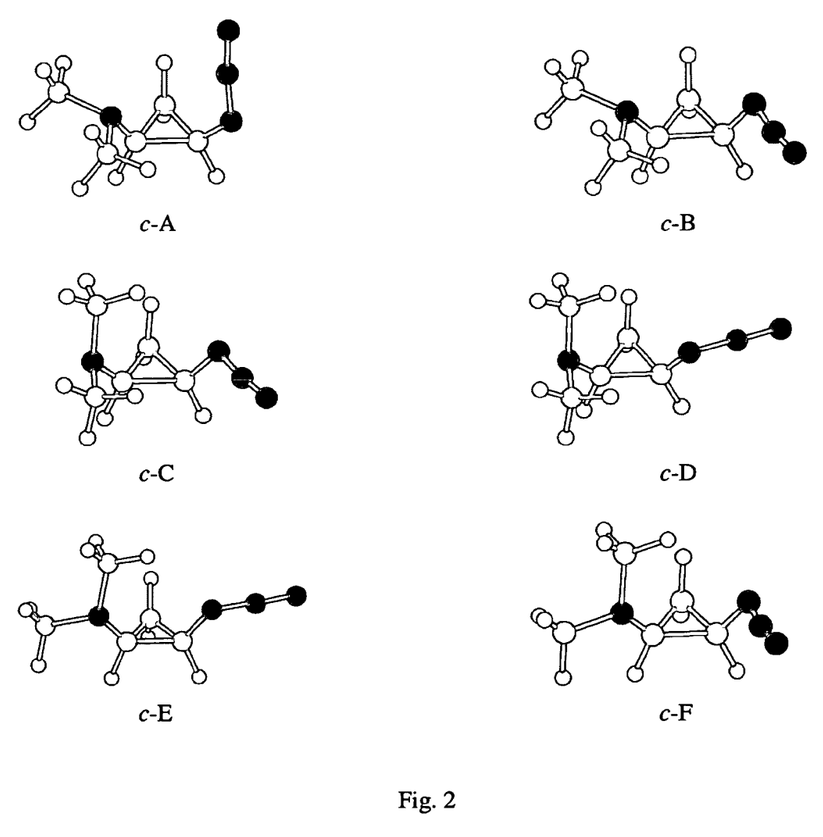
FIG. 2 depicts molecular structures of equilibrium cis-ADMCPA conformers, black circles denoting nitrogen atoms, gray circles denoting carbon atoms and white circles denoting hydrogen atoms.

FIGS. 1 and 2 show, respectively, the equilibrium trans-ADMCPA and cis-ADMCPA structures identified through the computations. The labeling scheme is chosen such that alphabetically adjacent conformers are nominally transformed into one another by a dihedral angle rotation about one bond. Conformers t-A and t-B are more than 4 kcal/mol lower in energy than the other conformers. The six trans conformers identified are all of the structures that can be constructed from combinations of observed geometric preferences. Based on a Boltzmann distribution calculated from trans conformer zero-point corrected energies, t-A (58%) and t-B (41%) populations will dominate a trans-ADMCPA sample at room temperature.

The six cis conformers identified are all of the structures that can be constructed from combinations of observed geometric preferences, and c-A and c-B are more than 4 kcal/mol lower in energy than the other four conformers. There is also a 1.0 kcal/mol difference between conformers c-A and c-B. Based on a Boltzmann distribution calculated from cis conformer zero-point corrected energies, c-A (82%) and c-B (18%) populations will dominate a cis-ADMCPA sample at room temperature.

Figure 3:
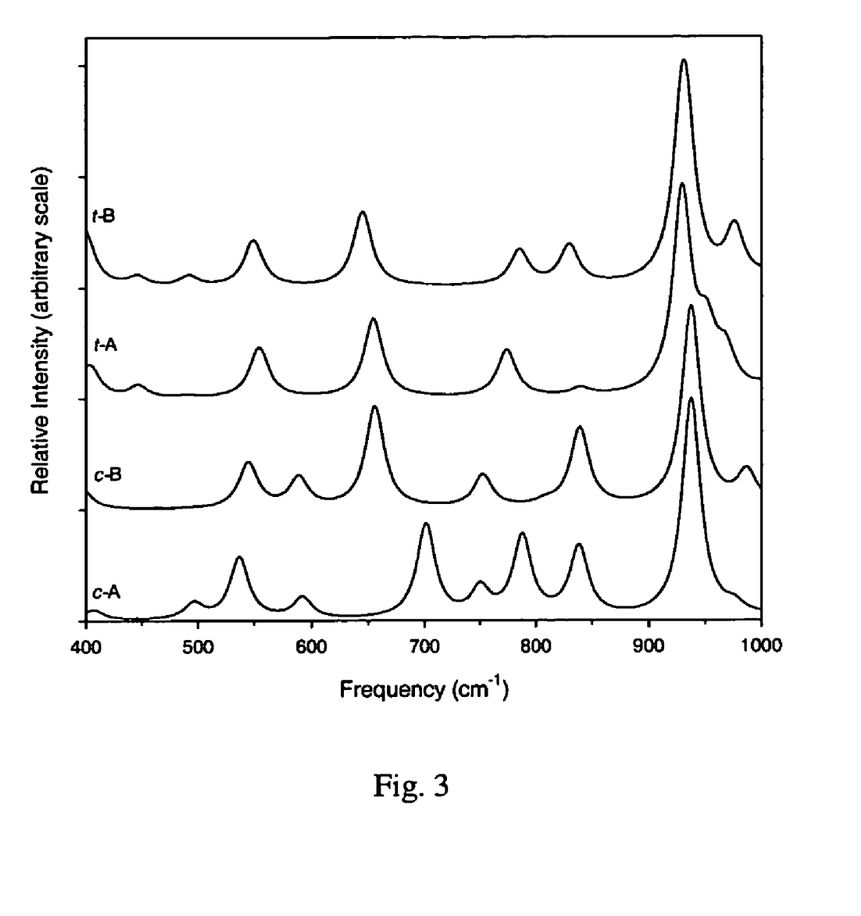
FIG. 3 is a simulation of mid-IR absorption intensity versus frequency for low energy trans-ADMCPA and cis-ADMCPA structures.

With 19 atoms and CS symmetry, all ADMCPA conformers have 51 normal modes. The predicted IR spectra based on modeling vibrational band contours (due to rotational line structure) with a Lorentzian lineshape, $$I(v) = \sum_j A_j \frac{\gamma/\pi}{(v_j - v)^2 + \gamma^2}$$

where $A_j$ is the integrated absorption for a transition to the $j^{th}$ normal mode and $\gamma$(equal 10 cm$^{-1}$) is the lineshape width at half-maximum, is shown in FIG. 3 for representative conformers c-A, c-B, t-A and t-B.

EXAMPLE 2

Computational Quantum Chemistry Results for 2-azido-N-methylcyclobutanamine (AMCBA)

Figure 4:
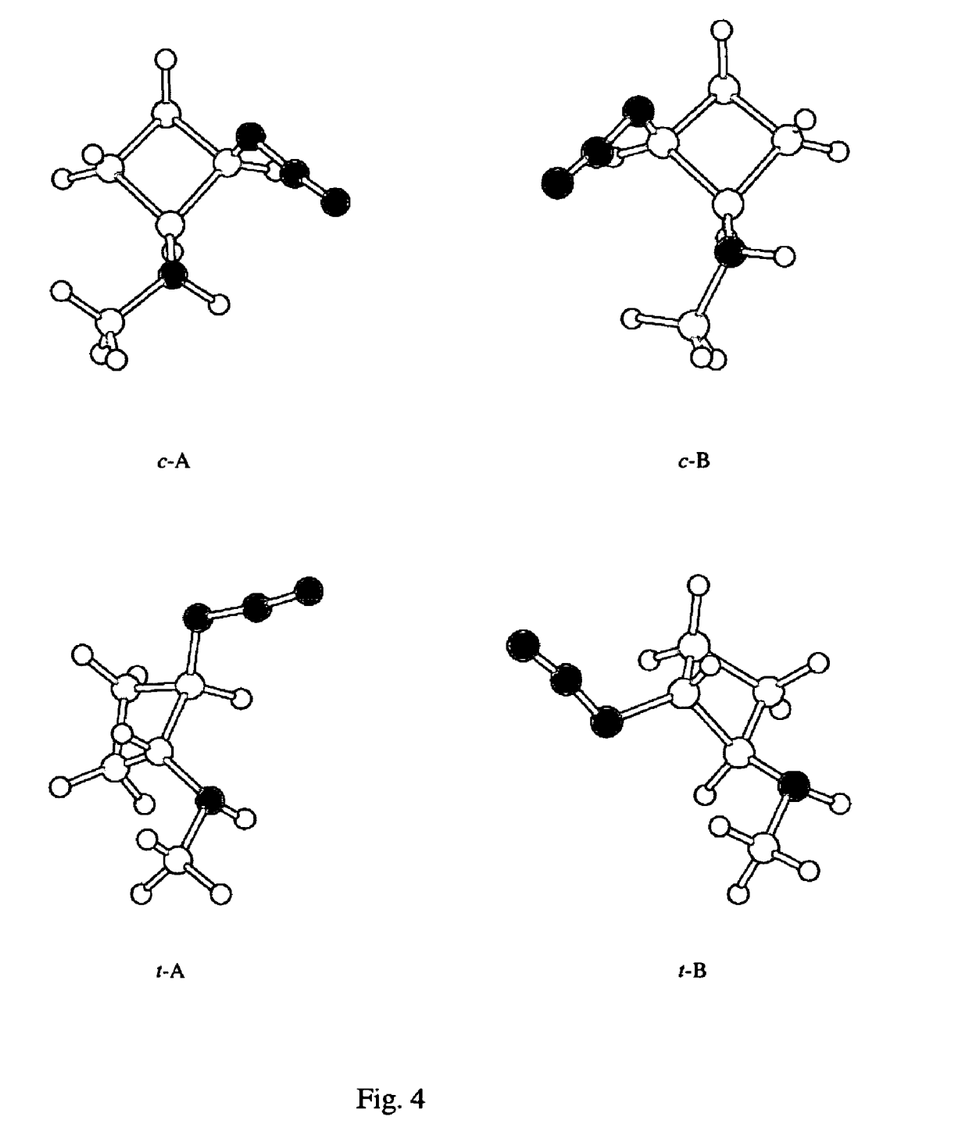
FIG. 4 depicts molecular structures of equilibrium 2-azido-N-methylcyclobutanamine (AMCBA) conformers, black circles denoting nitrogen atoms, gray circles denoting carbon atoms and white circles denoting hydrogen atoms.

The methods of Example 1 are repeated with the substitution of 2-azido-N-methylcyclobutanamine (AMCBA) for ADMCPA. Equilibrium AMCBA structures are shown in FIG. 4. Conformers shown in FIG. 4 were obtained via geometry optimizations from starting structures expected to be energetically favored based on the ADMCPA optimal structures. The cis isomers of AMCBA include a configuration with interacting amine and azide groups that is 1.0 kcal/mol lower in energy than otherwise similar conformers. Thus, a population dominated by a shielded configuration for the amine group is expected for the cis forms. Trans AMCBA allows closer proximity between the azido and amine groups (0.371 nanometers from the amine nitrogen to the middle nitrogen of the azide group) than in trans ADMCPA (0.429 nanometers for t-B).

EXAMPLE 3

Computational Quantum Chemistry of 2-azidocyclopentanamine (ACPA)

Figure 5:
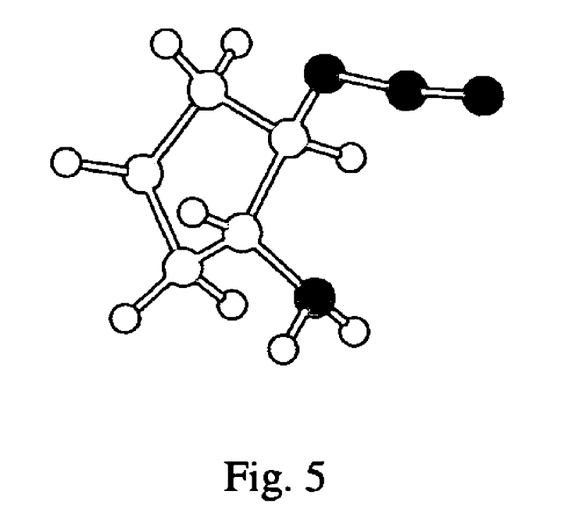
FIG. 5 depicts the molecular structure of an equilibrium trans-2-azidocyclopentanamine (ACPA) conformer, black circles denoting nitrogen atoms, gray circles denoting carbon atoms and white circles denoting hydrogen atoms.

The methods of Example 1 are repeated substituting the structure of 2-azidocyclopentanamine (ACPA) for ADMCPA. An equilibrium ACPA structure is shown in FIG. 5. Trans ACPA allows closer proximity between the azido and amine groups (0.316 nanometers) as compared to trans ADMCPA (0.429 nanometers for t-B).

EXAMPLE 4

Figure 6:
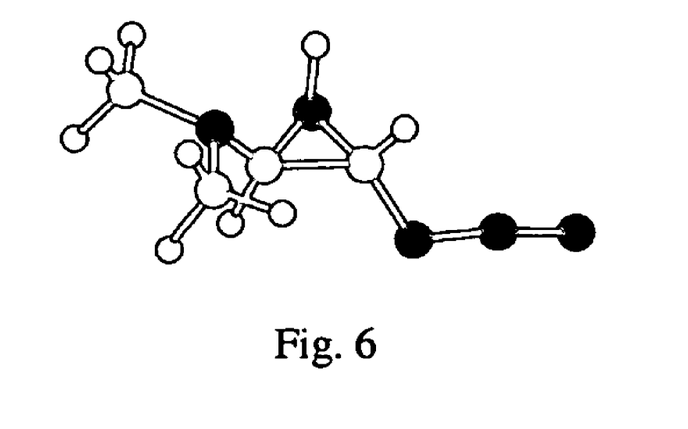
FIG. 6 depicts the molecular structure of an equilibrium trans-3-azido-2-dimethyl-aminoaziridine conformer, black circles denoting nitrogen atoms, gray circles denoting carbon atoms and white circles denoting hydrogen atoms.

Computational Quantum Chemistry Results for 3-azido-2-dimethylaminoaziradine The method of Example 1 was repeated with the substitution of the structure for 3-azido-2-dimethyl-aminoaziradine (ADMAA) for that of ADMCPA. An equilibrium conformer for trans-3-ADMAA is shown in FIG. 6.

EXAMPLE 5

ADMCPA Isomer Densities and Heats of Vaporization

In addition to the gas-phase properties detailed herein, condensed-phase densities and heats of vaporization for the representative inventive ADMCPA isomers are shown in comparison to prior art compounds in Table 1. Coupled with the predicted gas-phase heats of formation, such property predictions are employed to predict fuel performance in a propulsion system. The molecular mechanics method employed to predict densities and heats of vaporization is known. Table 1 compares the densities predicted for 2-azido-N-methylethanamine (MMAZ), DMAZ, and 2-azido-N-cyclopropylethanamine (CPAZ) with the inventive cis and trans forms of ADMCPA. Table 1 also presents estimates for the heats of vaporization predicted for MMAZ, DMAZ, and CPAZ for comparison with the inventive cis and trans forms of ADMCPA. The potential error associated with this approach is expected to be less than ±2 kcal/mol.

EXAMPLE 6

Ballistic Properties of ADMCPA Isomers

With estimates for condensed-phase heats of formation and densities from Example 5, specific impulse ($I_{SP}$) and density impulse ($D^*I_{SP}$) are calculated for MMAZ, DMAZ, CPAZ, and the inventive ADMCPA isomers upon combination with an oxidizer. Table 1 compares optimized $I_{SP}$ values from NASA-Lewis rocket calculations (B. J. McBride et al. "Computer Program for Calculation of Complex Chemical Equilibrium Compositions and Applications II. Users Manual and Program Description." NASA Reference Publication 1311, NASA Lewis Research Center, Cleveland, Ohio, 1996) for a system in which the oxidizer is an IRFNA "mixture". It is observed that the optimized $I_{SP}$ values for the aliphatic amine azides are nearly identical to each other, and less than 1% lower than the value obtained for MMH. Moreover, with higher densities than MMH, the aliphatic amine azides' $D^*I_{SP}$ values are predicted to be higher than that for MMH.

Those skilled in the art will appreciate from the foregoing description and examples that the broad teaching of the present invention can be implemented in a variety of forms. Therefore, while this invention has been described in connection with particular examples thereof, the true scope of the invention should not be so limited since other modifications will become apparent to one skilled in the art upon review of the specification and the following claims.

All patents and other publications cited herein are expressly incorporated by reference to the same extent as if each individual publication or patent were specifically and individually indicated to be incorporated by reference.

What is claimed is:

1. A compound of the formula:

where A is $CHR^1$, O, $CHR^1CHR^1$, $CHN(R^2)_2CH_2$, $CHR^1CHR^1CHR^1$, $NR^2CH_2CHR^1$, $CHR^1CH_2NR^2$, $CH_2NR^2CH_2$, $NR^2$, $NR^2CH_2$, $CH_2NR^2$, $CH_2O$, $OCH_2$, $OCH_2CH_2$, or $CH_2OCH_2$; $R^1$ in each occurrence is independently H or $N(R^2)_2$; $R^2$ in each occurrence is independently H, $CH_3$, or $CH_2CH_3$; $R^3$ is H, $N(R^2)_2$ where Z is CH or N; and a dashed bond denotes single bonds that when $R^3$ is $N(R^2)_2$, gives the compound a cis or trans orientation, wherein the compound contains at least one amino group and wherein said amino group is primary, secondary or tertiary.

2. The compound of claim 1 comprising a single amine group.

3. The compound of claim 1 where A is $CH_2$.

4. The compound of claim 3 where Z is CH, $R^3$ is $N(R^2)_2$.

5. The compound of claim 4 where $R^2$ is $CH_3$ in both occurrences.

6. The compound of claim 4 where $N(R^2)_2$ is cis to the $N_3$ group.

7. The compound of claim 4 where $N(R^2)_2$ is trans to the $N_3$ group.

8. The compound of claim 1 where A is selected from the group consisting of: $CHR^1CHR^1$, $NR^2CH_2$, $CH_2O$, and $OCH_2$.

9. The compound of claim 8 where A is $CH_2CH_2$.

10. The compound of claim 9 where Z is CH and $R^3$ is $N(R^2)_2$.

11. The compound of claim 10 where the $N(R^2)_2$ is cis to the $N_3$ group.

12. The compound of claim 10 where the $N(R^2)_2$ is trans to the $N_3$ group.

13. The compound of claim 1 where A is selected from the group consisting of $NR^2$ $CH_2CHR^1$, $CHR^1$, $CHR^1CH_2NR^2$, $CH_2NR^2CH_2$, $CHN(R^2)_2CH_2$, $CHR^1CH^1CHR^1$, $OCH_2CH_2$ and $CH_2OCH_2$ with the proviso that when A lacks a nitrogen atom then $R^3$ is $N(R^2)_2$.

14. The compound of claim 13 where Z is CH.

15. The compound of claim 1 where A is $CH_2CH_2CH_2$.

16. The compound of claim 15 where Z is CH, $R^3$ is $N(R^2)_2$.

17. The compound of claim 16 where $R^2$ in each occurrence is H.

18. The compound of claim 1 where A is selected from the group consisting of: $NR^2$, $NR^2CH_2$ or $CH_2NR^2$ and Z is CH.

19. The compound of claim 18 where A is $NR^2$ and $R^3$ is $N(R^2)_2$.

20. A propellant comprising: a compound according to claim 1 and a source for inducing reaction of said compound, said source selected from the group consisting of: an oxidant and an igniter.

21. The propellant of claim 20 wherein the source is an oxidant.

22. The propellant of claim 21 wherein the oxidant is selected from the group consisting of: liquid oxygen, hydrogen peroxide, nitric acid, nitrogen dioxide and inhibited red fuming nitric acid.

23. The propellant of claim 22 wherein said oxidant is inhibited red fuming nitric acid.

24. The propellant of claim 20 further comprising a gellant.

25. The propellant of claim 24 further comprising an additive selected from the group consisting of: amine-nitrate salts, quaternary ammonium salts, carbon, aluminum, silicon, boron and tungsten.

* * * * *